US00PP25374P3

(12) United States Plant Patent
Schoone

(10) Patent No.: US PP25,374 P3
(45) Date of Patent: Mar. 24, 2015

(54) *PHALAENOPSIS* ORCHID PLANT NAMED 'STREETWISE'

(50) Latin Name: ***Phalaenopsis* hybrid**
Varietal Denomination: Streetwise

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 102 days.

(21) Appl. No.: 13/986,328

(22) Filed: Apr. 22, 2013

(65) Prior Publication Data

US 2013/0291256 P1 Oct. 31, 2013

Related U.S. Application Data

(60) Provisional application No. 61/638,004, filed on Apr. 25, 2012.

(30) Foreign Application Priority Data

Apr. 26, 2012 (NL) ..... PBR OPS904

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Annette Para
(74) *Attorney, Agent, or Firm* — Foley & Lardner LLP; Sunit Talapatra

(57) ABSTRACT

A new and distinct *Phalaenopsis* plant named 'Streetwise' particularly characterized by flowers which are white/green with purple marks; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Streetwise'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Streetwise'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Streetwise' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Streetwise' originated from a cross made by the inventor in 1999 in Strengweg, Heemskerk, The Netherlands. The female or seed parent is the *Phalaenopsis* cultivar designated 'Sunrise Delight', unpatented. The male or pollen parent is the *Phalaenopsis* cultivar designated 'Love Rosa', unpatented. The new *Phalaenopsis* 'Streetwise' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Streetwise', which in combination distinguish this *Phalaenopsis* as a new and distinct cultivar:

1. flowers which are green/white with purple marks;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Streetwise', the female parent 'Sunrise Delight' has yellow flowers and the male parent 'Love Rosa' has dark pink colored flowers, whereas the flowers of 'Streetwise' are green/white with purple marks.

Presently, there is no other commercial cultivar to which 'Streetwise' can be meaningfully compared.

BRIEF DESCRIPTION OF THE PHOTOGRAPHS

The accompanying photographs illustrate the overall appearance of the new *Phalaenopsis* 'Streetwise' showing the colors as true as is reasonably possible with colored reproductions of this type. Colors in the photographs may differ slightly from the color values cited in the detailed botanical description, which accurately describe the color of 'streetwise'.

DETAILED BOTANICAL DESCRIPTION

Figure 1:
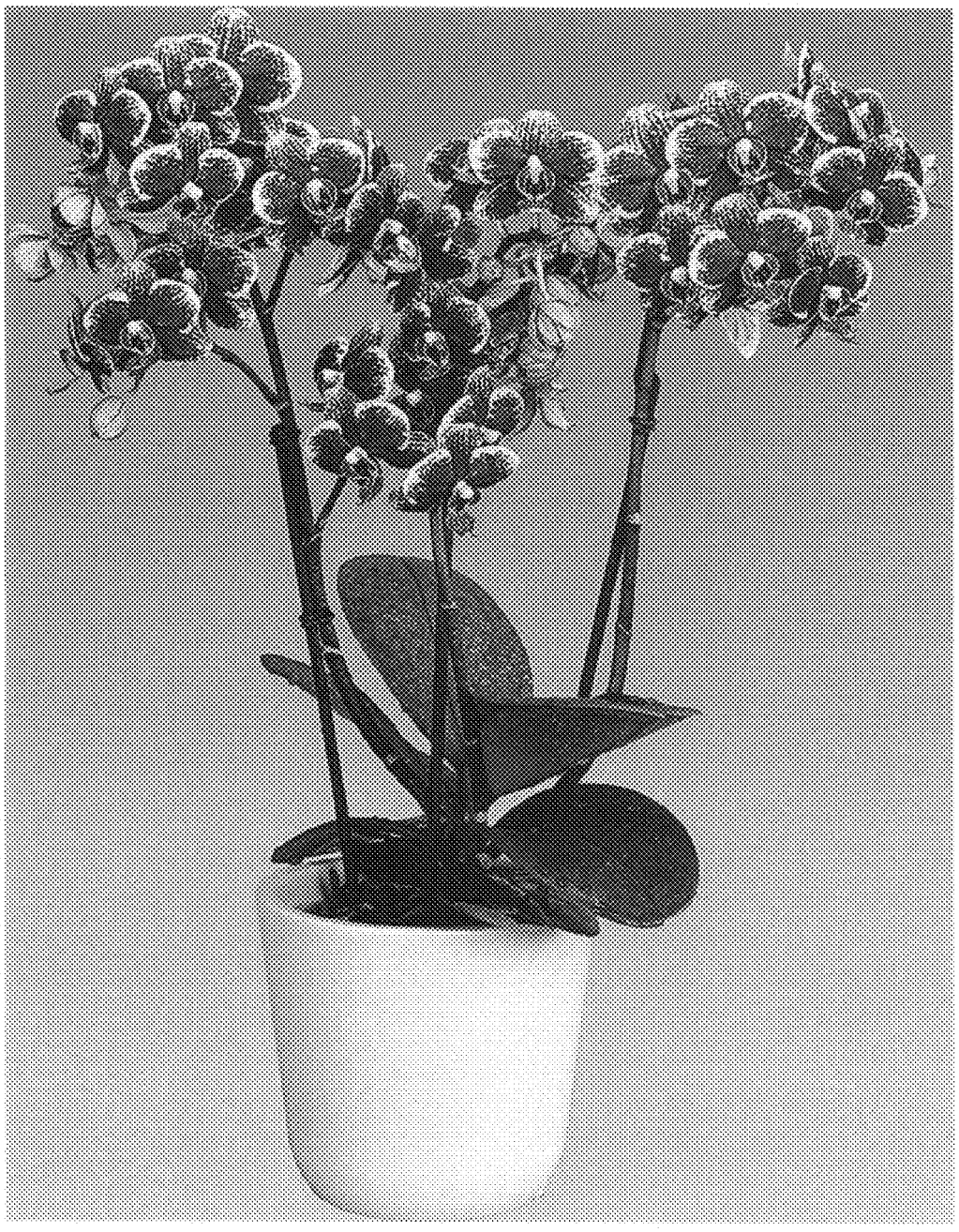
FIG. 1 shows a side view perspective of a typical flowering plant of 'Streetwise' in a 12 cm pot, at 16 months of age.

The new *Phalaenopsis* cultivar 'Streetwise' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Streetwise' as grown in a greenhouse in Strengweg, Heemskerk, The Netherlands, under conditions which closely approximate those generally used in commercial practice. Initially, the ideal temperature to grow plants of 'Streetwise' is 27° C. during the day and at night. Then, during the flowering phase of 'Streetwise', the ideal growing temperature is 20-22° C. during the day and 18° C. at night. Light levels for growing 'Streetwise' are a minimum of 5,000 lux and a maximum of 10,000 lux. A balanced fertilizer with level of 200 ppm N, 87 ppm P, 168 ppm K is applied. Duration of growth of 'Streetwise' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Streetwise' plants described is 12 months after potting.

Classification:

*Botanical.*—*Phalaenopsis* hybrid.

Parentage:

*Female or seed parent.*—*Phalaenopsis* cultivar designated 'Sunrise Delight', unpatented.

*Male or pollen parent.*—*Phalaenopsis* cultivar designated 'Love Rosa', unpatented.

Propagation:

*Type.*—Tissue culture.

*Rooting habit and description.*—Fleshy; approximately 3 mm-6 mm wide and green in color (RHS 191B); freely branching. It takes 12 weeks for plants growing in tissue culture to initiate roots.

Plant:

*Size at maturity.*—Height: about 43 cm. Spread: about 27 cm.

*Growth habit.*—Small; dark-green leaves and a relatively large raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is a little bit round and asymmetric.

*Texture* (*upper & underside*).—Smooth and leathery.

*Pubescence.*—3 to 4 pairs of leaves.

*Mature leaf length.*—About 9 to 15 cm.

*Mature leaf width.*—About 5 to 7 cm.

*Mature leaf thickness.*—About 2 mm.

*Mature leaf color.*—Upper side: green (RHS 137A). Under side: green (RHS 137D).

*Leaf base.*—Acute.

*Margin.*—Entire.

*Venation.*—Pattern: parallel. Color of midvein: upper side: green (RHS 137A). under side: green (RHS 137D).

Raceme:

*Quantity per plant.*—About 1 to 3.

*Number of flowers per raceme.*—About 10 to 15.

*Length.*—About 31 cm.

*Diameter.*—About 3 to 6 mm.

*Strength.*—Strong.

*Aspect.*—Upright.

*Texture.*—Glabrous and smooth.

*Color.*—Brown (RHS N200A) and some yellow/green (RHS 144A).

*Internode.*—Length: about 28 to 36 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 17 mm. Diameter (at midpoint): about 16 mm. Shape: egg-shaped/oval. Color: yellow/green (RHS 145C) with some purple (RHS 59A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
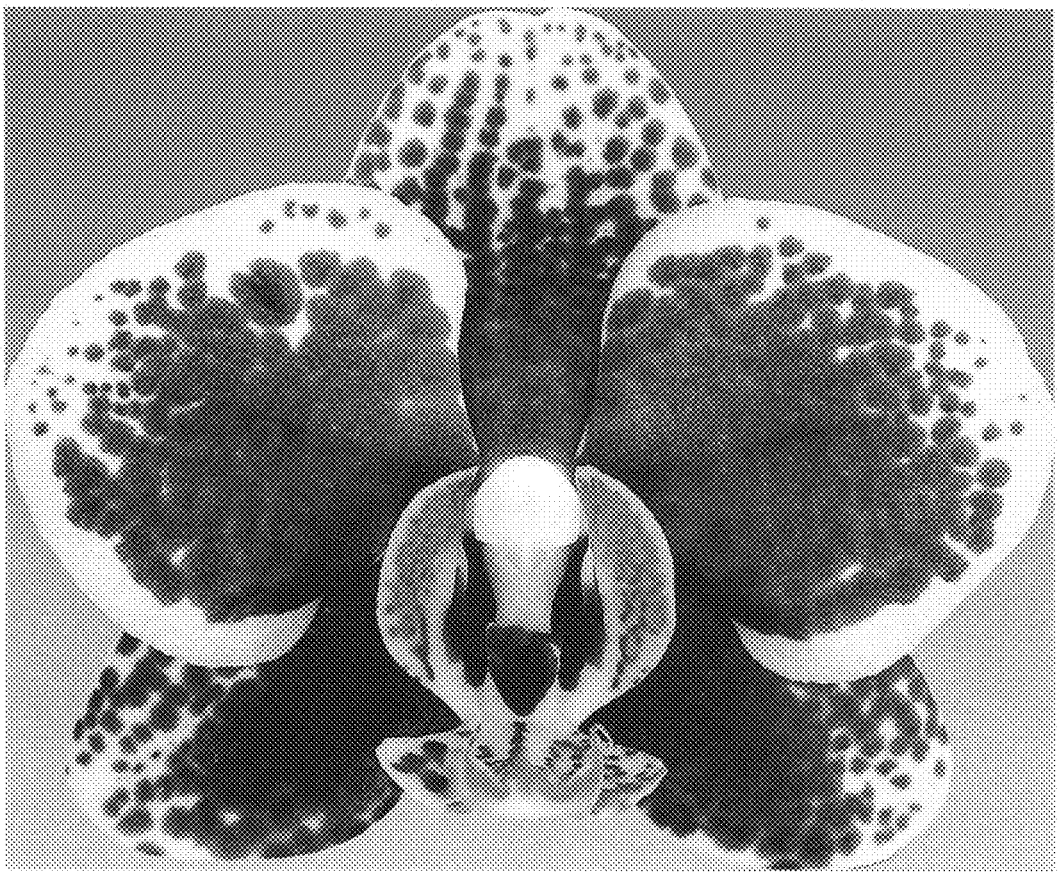
FIG. 2 shows a close-up view of the typical buds and flowers of 'Streetwise'.
Figure 3:
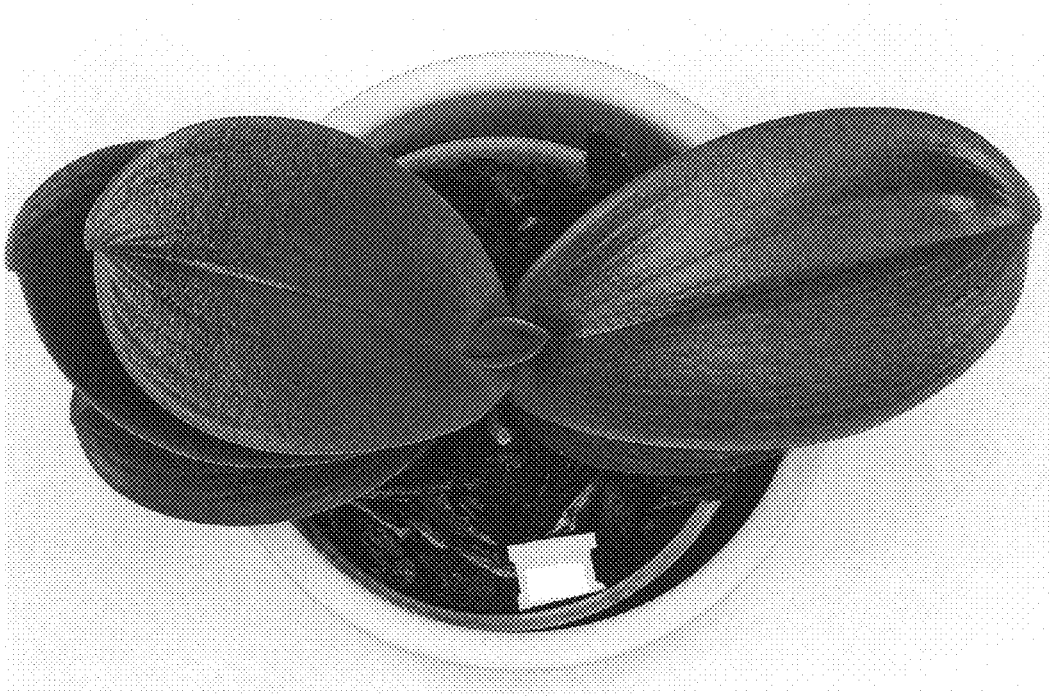
FIG. 3 shows a close-up view of the typical leaves of 'Streetwise'.

*Flower*.—Rate of opening: Flowers fully opened about 2 to 3 days after petal and sepal separation. Orientation at opening: slanted upward and outward. Shape: see FIG. 2. Size: Height: about 34 mm to 55 mm. Diameter: about 44 mm to 64 mm. Depth of tube: about 8 mm.

*Petals*.—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate, little triangular and weakly cupped. Apex: oval. Margin: entire and weakly undulate. Base broadly ovate. Length: about 19 mm to 33 mm. Width: about 20 mm to 30 mm. Texture: Upper surface: smooth and satiny. Under surface: smooth and satiny. Color (when fully opened): upper side: Green/white (RHS 157C) with purple marks in different shades (RHS 59A, RHS 71A and RHS N77A). Under side: Green/white (RHS 157B). The midvein is purple (RHS 72B) and on the edges some purple (RHS 79D).

*Labellum*.—Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: oval. Length: about 13 mm. Width (not flattened): about 14 mm. Texture: Upper and under surface: smooth and satiny. Color (when fully opened): Midlobe: upper surface: at the base yellow (RHS 13B), in the middle a purple stripe (RHS N79A). Some purple spots/stripes (RHS 72A and RHS 59A). The edge and in the middle some white (RHS NN155C) Under surface: Main color is white (RHS NN155B). At the base on the edges some yellow (RHS 13B) and some purple spots (RHS 59A and RHS N79A). Also a few purple stripes (RHS 72A). Lateral lobes: upper surface: At the base some red/purple (RHS 59A/N79A) then some white (RHS NN155B) and after that some purple (RHS 72A). The edges are yellow (RHS 13B). Under surface: Main color is white (RHS NN155A). the inner edges are yellow (RHS 13B) with at the base a small purple edge (RHS N79A). Chirri: small and thin (about 1 to 2 mm) and more than 2; color: first purple (RHS 72A) then white (RHS NN155B). Pestle (Callosities): Length: about 3 mm. Width (not flattened): about 4 mm. Color: purple (RHS N187A) on top and the edges are white (RHS 155A) and yellow (RHS 12C).

*Sepals*.—Arrangement: Outer whorl comprises 3 sepals. Overall shape: elliptical and weakly cupped. Margin: entire and weakly undulate. Length: about 21 to 33 mm. Width: about 17 to 26 mm. Apex: dorsal: round with a notch; lateral: round. Texture: Upper and under surface: smooth and satiny. Color (when fully opened): upper surface: green/white (RHS 157C) with purple marks in different shades (RHS 59A, RHS 71A and RHS N77A); Under surface: yellow/green (RHS 145C and RHS 145B) with at the base some green/white (RHS 157A), ate the edges some RHS 79D and a small line of red/purple (RHS 59A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 8 mm. Diameter: about 5 mm. Color: white (RHS NN155B) with a haze of purple (RHS 72B).

*Pollinia*.—Quantity: two. Diameter: about 1 mm. Color: yellow/orange (RHS 23B).

*Ovary*.—Length: about 3 mm. Diameter: about 2 mm. Color: white (RHS NN155B).

*Pedicel*.—Length: about 28 mm to 36 mm. Diameter: about 3 mm. Texture: glabrous and smooth. Color: Close to the flower it's green/white (RHS 157A) which turns into yellow/green (RHS N144D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Streetwise', as illustrated and described herein.

* * * * *